United States Patent [19]

Kerfoot

[11] 4,270,922
[45] Jun. 2, 1981

[54] INTEGRATING CORROSION MONITOR

[75] Inventor: William B. Kerfoot, Falmouth, Mass.

[73] Assignee: K-V. Associates, Inc., Falmouth, Mass.

[21] Appl. No.: 98,874

[22] Filed: Nov. 30, 1979

[51] Int. Cl.³ .......................................... G01N 17/00
[52] U.S. Cl. ..................................... 23/230 C; 422/53
[58] Field of Search .......................... 23/230 C, 230 A; 422/53; 73/86

[56] References Cited

U.S. PATENT DOCUMENTS

| | | | |
|---|---|---|---|
| 2,374,088 | 4/1945 | Fontana et al. | 23/230 C |
| 2,972,248 | 2/1961 | Gerhardt | 23/230 C |
| 3,259,461 | 7/1966 | Griffin, Jr. et al. | 422/53 X |
| 3,734,690 | 5/1973 | Kolodney et al. | 23/230 C |
| 4,043,178 | 8/1977 | Winslow, Jr. | 422/53 X |

Primary Examiner—Ronald Serwin
Attorney, Agent, or Firm—Diller, Ramik & Wight

[57] ABSTRACT

This disclosure relates to a method of and apparatus for determining the corrosion rate of metal by liquid flowing in a metallic pipe system by continuously bleeding off upstream and downstream liquid portions from a metallic pipe at predetermined rates for predetermined time periods and filtering therefrom both heavy metals and particulate metals, determining the rate of solution corrosion and cavitation-erosion of the metal from the amount of heavy metals and particulate metals, respectively, filtered from the upstream and downstream bled-off liquid portions, and integrating the difference between the upstream and downsteam determinations to obtain the corrosion rate of the metallic pipe system.

20 Claims, 5 Drawing Figures

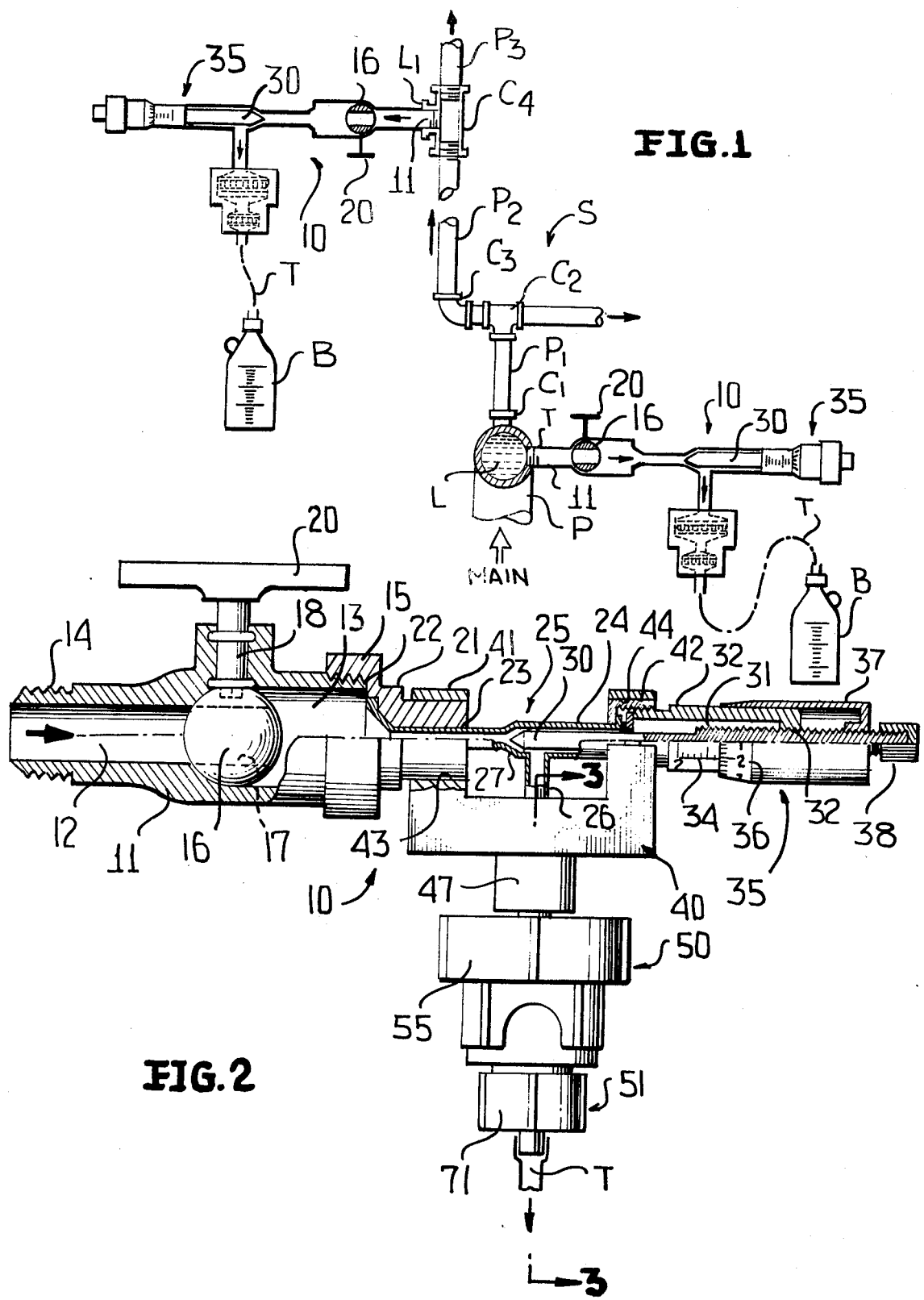

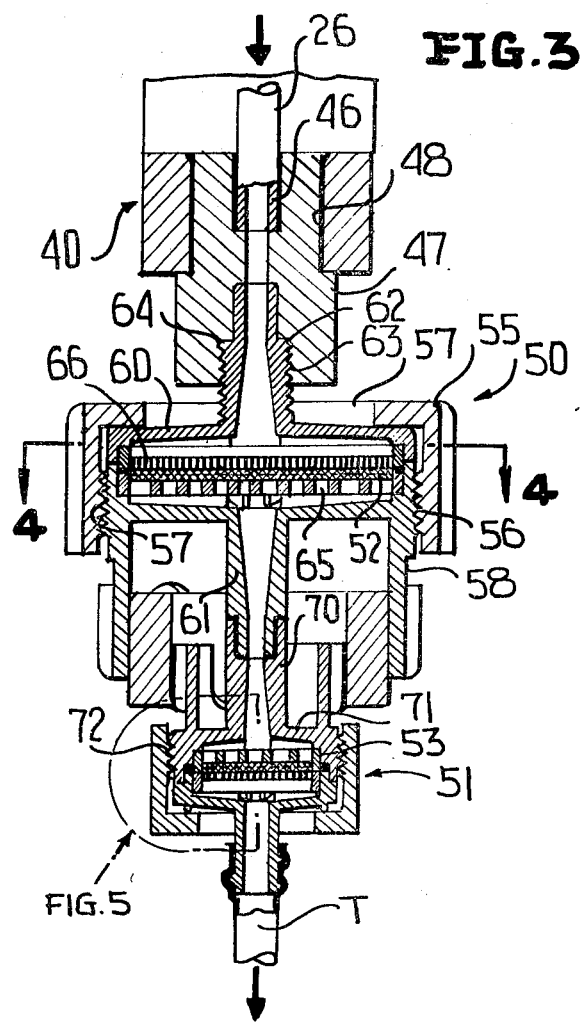
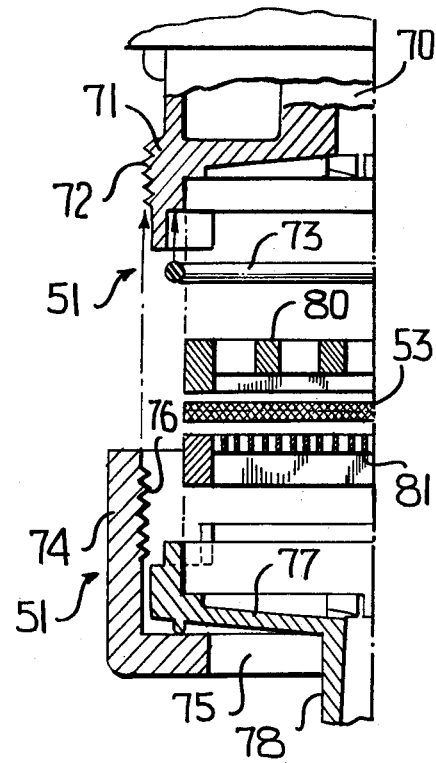
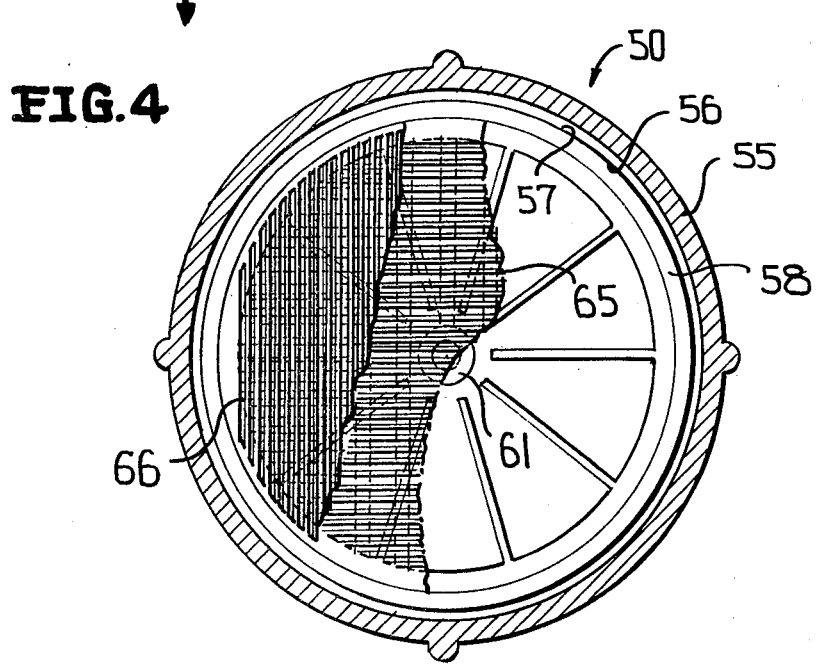

INTEGRATING CORROSION MONITOR

This disclosure is directed to an apparatus for and a method of determining the corrosion rate of a liquid service system, such as a conventional drinking water pipeline system, although it is equally applicable to most any other type of metallic pipe systems which are subject to erosion and/or corrosion by the liquid flowing therethrough.

One relatively reliable way to determine the corrosion rate of a metal is to expose the metal to the environment under service conditions. Therefore, if one were to determine the rate of erosion and solution corrosion occuring in joints and main piping, such would be continuously monitored for a relatively long period of time, but such procedure would obviously be slow and costly, and thus has been substituted for by laboratory approximations. However, in keeping with the present apparatus and method continual sampling of the metal contents of water can be monitored at upstream and downstream points of a particular liquid system, and the integrated difference between the upstream and downstream readings is proportional to the corrosion rate of the system being monitored. In this way appropriate steps can be taken to assure maximum suppression of corrosion by, for example, the addition of appropriate corrosion inhibitors to the liquid system.

It should be noted that contrary to initial impressions, extremely clean water at the source of supply does not assure users of the highest quality of drinking water at their taps. For example, brass suffers more attack in distilled water than in acid and soft, low pH waters with little mineral content tend to be highly corrosive to some metals and react with a variety of alloys and plastics used in the pumps, pipe fittings and reservoirs of distribution and plumbing systems. Studies have indicated that reactions, particularly of soft, low-pH waters, with materials of distribution systems often have produced much greater concentration of iron, copper, zinc, lead and cadmium at the tap than those at the treatment plant or pumping station and/or reservoir. Obviously, in keeping with the present apparatus and/or method appropriate controls can be accomplished by pH adjustment through frequent monitoring to assure maximum suppression of corrosion with cost-effectiveness of inhibitor addition. The latter (corrosion inhibitor addition) to city water has been shown to decrease the weight loss of piping systems to $\frac{1}{4}$-$\frac{1}{2}$ that observed with uninhibited water. Thus, in keeping with the present invention, one can determine with relative precision the particular rate of corrosion to which a liquid distribution and/or plumbing system is subject to and appropriate action can be taken on a continuous basis to preclude or limit such corrosion.

The apparatus of this invention includes a totally nonmetallic device provided with a threaded conduit for connection to a metallic pipe of a system which is to be monitored and having an adjustable metering valve for variably selectively adjusting the rate of flow of the bled-off liquid portion from the liquid system. The bled-off portion is fed through a pair of filters from which the cavitation-erosion rate and/or solution corrosion rate of the metal of the pipe system by the liquid can be determined.

Preferably, such devices are tapped into the system which is being monitored at upstream and downstream points with the readings compared and integrated to determine the corrosion rate of the overall system which can then be followed by appropriate action to suppress the corrosion thereof and, thus, decrease the weight loss of the piping system.

With the above and other objects in view that will hereinafter appear, the nature of the invention will be more clearly understood by reference to the following detailed description, the appended claims and the several views illustrated in the accompanying drawings.

IN THE DRAWINGS:

FIG. 1 is a schematic view of a distribution and/or plumbing system, and illustrates two monitors constructed in accordance with this invention connected at upstream and downstream points of the system.

FIG. 2 is a side elevational view partially broken away and shown in cross section of one of the devices of FIG. 1, and illustrates a main on-off valve, an adjustable metering valve, and a pair of filters for filtering particulate metal and metal ions.

FIG. 3 is a sectional view taken generally along line 3—3 of FIG. 2, and illustrates two chambers of the filters each having a pair of porous walls between which is housed the filters for filtering particulate and dissolved metals.

FIG. 4 is an enlarged sectional view taken generally along line 4—4 of FIG. 3, and illustrates two of the porous walls between which is sandwiched a filter element.

FIG. 5 is a fragmentary exploded view of the encircled portion of FIG. 3, and illustrates details of the housing for one of the pair of filters, namely, the metallic ion filter.

Reference is first made to FIG. 1 which schematically illustrates a liquid distribution and/or plumbing system generally designated by the reference character S which may be, for example, a city water distribution system having a plurality of pipes P, P1, P2, P3, etc., and appropriate joints or couplings C1, C2, C3, C4, etc., all of which are constructed from metallic material, such as cast iron, bronze, copper or the like. The metallic pipe P may be considered to be the upstream or main line of the overall system S, whereas the pipe P3 might well be located a substantial distance downstream from the main pipe P. However, since the various pipes P1 through P3 and the joints or connectors C1 through C4 associated therewith are all constructed from metallic material they are subject to corrosion or erosion by liquid L, such as water, flowing therethrough. Obviously, the greater degree of erosion or corrosion the greater the weight loss of the metal from the overall pipe system S and, hence, the more rapid its destruction and attendant replacement with corresponding added costs. With this thought in mind, the purpose of the invention is to monitor on a relatively continuous basis the amount of metallic corrosion and/or erosion in order that appropriate steps might be taken to reduce the same by, for example, adding appropriate corrosion inhibitors to the liquid or water L. The monitoring is accomplished by corrosion and/or erosion monitors, devices or apparatus, generally designated by the reference numeral 10 (FIG. 2) which are constructed throughout from nonmetallic material and are appropriately connected to upstream and downstream points of the system S, as is clearly illustrated in FIG. 1. The corrosion monitor 10 (FIG. 2) includes conduit means in the form of a fitting 11 having a bore 12 and a counterbore 13, the latter of which are respectively exteriorly threaded at 14, 15. The threaded end portion 14 of each of the corrosion monitors 10 is threaded into a tapped bore, such as the tapped bore T of the main pipe P of FIG. 1, or might simply be threaded into a normally closed threaded leg L1 of a conventional coupling, such as the T-coupling C4 of FIG. 1.

The fitting 11 carries a ball valve 16 which includes a conventional bore 17 with the valve 16 being connected to a stem 18 which is in turn connected to a handle 20. The ball valve 16 is in its open position such that liquid introduced into the bore 12 will flow through the bore 17 and into the counterbore 13.

Another fitting 21 having an internal thread 22 is coupled to the fitting 11 by simply being threaded to the thread 15 thereof. The fitting 21 carries a conduit of a generally T-shaped configuration which is designated by the reference numeral 25. The conduit 25 is preferably, though not necessarily constructed from transparent material, such as plastic or glass, and includes opposite conduit arm portions 23, 24 and a depending leg conduit portion 26 therebetween. A portion 27 between the arm conduit portions 23, 24 is tapered to receive a pointed needle 30 of a variably adjustable needle valve or needle valve means 35. The needle 30 includes a threaded end portion 31 threaded in a threaded bore 32 of a housing 33 having graduations 34 which are adapted for association with graduations 36 of a handle 37 which is secured to the threaded end portion 31 of the needle 30 by a fastening nut 38. The handle 37 is simply rotated in either a clockwise or a counterclockwise direction to move the needle 30 as desired to regulate the flow of the liquid L from the counterbore 13 and the arm conduit portion 23 through the conical portion 27 and into the leg conduit portion 26 for subsequent filtering, as will be described more fully hereinafter.

A generally bifurcated frame 40 is secured by respective arms 41, 42 and their respective apertures or bores 43, 44 to the fitting 21 and the adjustable valve means 35, respectively. The leg conduit portion 26 is seated in a bore 46 (FIG. 3) of a fitting 47 which is in turn seated in a bore 48 of the bifurcated arm 40. The fitting 47 has suspended therefrom a pair of housing 50, 51 which receive respective filter means 52, 53 for filtering particulate metallic and dissolved metal or metal ions from liquid L which is bled from the system S, as will be described more fully hereinafter.

The housing 50 includes a cover 55 having an internal thread 56 and a circular aperture 57 with the internal thread 56 being threadedly connected to an external thread 57 of a housing 58 which supports another housing 60. The housings 58, 60 have oppositely directed tubular portions 61, 62, the latter of which is externally threaded at 63 and is thus threadedly received and connected to an internally threaded bore 64 of the tubular fittings 47. A pair of circular porous walls or apertured walls 65, 66 are carried by the respective housings 58, 60 in spaced relationship to each other and the filter means 52 is held in sandwich relationship between the porous or apertured walls 65, 66. Thus, any liquid flowing downwardly through the leg conduit portion 26 and into the housing 60 passes through the porous wall 66, the filter means 52, the porous wall 65, and then passes outwardly from the housing 58 through the tubular port 61. While passing through the filter means 52, any metallic particles or particulate metal is collected by the filter means 52 and is thereafter subject to analysis as will be described more fully hereinafter. The filter means 52 may be, for example, a typical filter known in the trade by the trademark NUCLEPORE filter.

The housing 51 for the filter means 53 likewise includes a tubular portion 70 coupled to the tubular portion 61 and in part defining a housing 71 (FIG. 5) having an external thread 72 and an interior (unnumbered) for receiving a gasket 73. Another housing or wall 74 having a circular opening 75 carries a thread 76 for coupling to the thread 72 of the housing 71. Another wall or housing 77 having a tubular outlet 78 is received within the wall 74 and between the housings or walls 71, 77 are disposed porous or apertured walls 80, 81 between which is sandwiched the filter means 53 (FIG. 5). The filter means 53 is of the type disclosed in U.S. Pat. No. 3,877,878 in the name of William B. Kerfoot et al. issued on Apr. 15, 1975, and the function thereof is to filter from liquid L passing through the filter means 53 metallic or metal ions for subsequent analysis.

After the liquid L has passed through the filter means 52, 53, the same is led by the tubular outlet 78 to a suitable flexible tube T (FIGS. 1 and 3) to a container or bottle B which may have appropriate volumetric graduations (unnumbered) thereon.

Insofar as the operation of the corrosion monitor 10 is concerned, the same is relatively straightforward and is accomplished by first mounting one or more of the monitors 10 in the manner illustrated in FIG. 1. Obviously, the pressure is shut-off in the particular portion of the system S to which the monitors 10, 10 are connected before the same are connected, but once this is accomplished, the valve 16 can be closed and pressure reestablished in the system S. Thereafter, each of the needles 30 can be adjusted to develop a predetermined flow rate by simply rotating the handle 37 and establishing the flow rate by the associated graduations 34, 36 which preferably represent flow in milliliters per minute or fractions thereof. Since the various pipes P through P3 have varying diameters, the flow rates of the liquid L therethrough may vary, and thus the rate of flow through the leg conduit portion 26 of the various corrosion monitors 10 in the lines, pipes or couplings may not be identical to each other but should at least be proportional for ease of subsequent analysis. Once the valves 35 have been adjusted and the balls 16 open, the liquid L will flow through the filters 52, 53 in a predetermined flow rate and the metallic particles and metallic ions, respectively, will be collected thereby with the discharge liquid being collected in the graduated bottles B, B. Thereafter, after a predetermined time period, the valves 16 are closed, the filters 52, 53 are removed from each of the monitors 10, 10 and the volume of water associated with each bottle B, B is noted and analyzed along with the filters.

As a typical example, if each of the corrosion monitors 10, 10 of FIG. 10 are set to their respective micrometer valves 35 for a flow rate of 1 ml/minute. This will result in a total flow of 1.4 liters over a 24-hour period. After, for example, 24 hours have passed, the filters 52, 53 can be removed from each of the monitors 10, 10 and, of course, the amount of liquid in the bottles B, B will be 1.4 liters. Analysis of the total metal content of each filter 52 is an indication of the cavitation-erosion rate, while the analysis of the total dissolved metal of each filter 53 through argon emission plasma or atomic absorption spectrometry provides an indication of the metal removed through solution corrosion. The integrated difference between the upstream and downstream readings is proportional to the corrosion rate of the overall system S. Once this is known, plant personnel can then institute preventive maintenance to provide major savings, improve plant efficiency, predict service schedules more accurately and select optimal water treatment and service line piping.

Although only a preferred embodiment of the invention has been specifically illustrated and described herein, it is to be understood that minor variations may be made in the apparatus or in the method of without departing from the spirit and scope of the invention, as defined in the appended claims.

I claim:

1. A method of determining the rate of solution corrosion of metal by liquid flowing through a metallic pipe comprising the steps of
   (a) continuously bleeding off a portion of the liquid from the pipe at a predetermined rate of flow for a predetermined period of time,
   (b) continuously filtering from the bled-off liquid portion heavy metals during said predetermined period of time, and
   (c) determining the rate of solution corrosion of the metal by the liquid from the amount of heavy metals filtered from the liquid during the predetermined time period at the predetermined flow rate.

2. The method as defined in claim 1 including the step of collecting the after-filtered bled-off liquid portion during said predetermined period of time.

3. A method of determining the rate of cavitation-erosion of metal by liquid flowing through a metallic pipe comprising the steps of
   (a) continuously bleeding off a portion of the liquid from the pipe at a predetermined period of time,
   (b) continuously filtering from the bled-off liquid portion particulate metals during said predetermined period of time, and
   (c) determining the rate of cavitation-erosion of the metal by the liquid from the amount of particulate metals filtered from the liquid during the predetermined time period at the predetermined flow rate.

4. The method as defined in claim 3 including the step of collecting the after-filtered bled-off liquid portion during said predetermined period of time.

5. A method of determining the rate of solution corrosion and the rate of cavitation-erosion of metal by liquid flowing through a metallic pipe comprising the steps of
   (a) continuously bleeding off a portion of the liquid from the pipe at a predetermined rate of flow for a predetermined period of time,
   (b) continuously filtering from the bled-off liquid portion heavy metals and particulate metals during said predetermined period of time,
   (c) determining the rate of solution corrosion of the metal by the liquid from the amount of heavy metals filtered from the liquid during the predetermined time period at the predetermined flow rate, and
   (d) determining the rate of cavitation-erosion of the metal by the liquid from the amount of particulate metals filtered from the liquid during the predetermined time period at the predetermined flow rate.

6. The method as defined in claim 5 including the step of collecting the after-filtered bled-off liquid portion during said predetermined period of time.

7. A method of determining the corrosion rate of metal by liquid flowing in a metallic pipe system comprising the steps of
   (a) continuously bleeding off an upstream portion of liquid from a metallic pipe of the system and continuously bleeding off a downstream portion of liquid from a metallic pipe of the system at predetermined rates of flow for predetermined periods of time which are equal or proportional to each other,
   (b) continuously filtering from the upstream and downstream bled-off liquid portions heavy metals and particulate metals during said predetermined periods of time,
   (c) determining the rates of solution corrosion of the metal by the liquid from the amount of heavy metals filtered from the upstream and downstream bled-off liquid portions during the predetermined time periods at the predetermined flow rates,
   (d) determining the rate of cavitation-erosion of the metal by the liquid from the amount of particulate metals filtered from the upstream and downstream bled-off liquid portions during the predetermined time periods at the predetermined flow rates, and
   (e) integrating the difference between the upstream and downstream determinations of steps (c) and (d) to obtain the corrosion rate of the metallic pipe system.

8. The method as defined in claim 7 including the step of collecting the after-filtered bled-off liquid portions during said predetermined periods of time of both the upstream and downstream bled-off liquid portions.

9. The method as defined in claim 7 wherein the periods of time of bled-off are the same for the upstream and downstream bled-off liquid portions.

10. Apparatus for bleeding off a portion of liquid from a metallic pipe and analyzing the metallic contents of the liquid comprising conduit means for connection to and for bleeding a portion of liquid from a metallic pipe, adjustable metering valve means for variably selectively adjusting the rate of flow of the bled-off liquid portion through said conduit means, and filter means downstream of said valve means for filtering metallic contents from the bled-off liquid portion whereby the amount of filtered metallic contents can be analyzed and utilized in conjunction with a known rate of flow to determine the cavitation erosion rate and/or solution corrosion rate of the metal by the liquid.

11. The apparatus as defined in claim 10 including another valve means upstream of said adjustable metering valve means for opening and closing fluid communication between an associated pipe and said adjustable metering valve means.

12. The apparatus as defined in claim 10 wherein said filter means filters particulate metal from the bled-off liquid portion.

13. The apparatus as defined in claim 10 wherein said filter means filters ions of at least one heavy metal.

14. The apparatus as defined in claim 10 wherein said filter means separately filters particulate metal and ions of at least one heavy metal.

15. The apparatus as defined in claim 10 wherein said conduit means includes a generally T-shaped conduit portion defined by an arm conduit and a leg conduit joined to said arm conduit medially of ends of the latter, said leg conduit being in fluid communication with said filter means, and said adjustable metering valve means being disposed to adjust the rate of flow of the bled-off liquid portion between one of said arm conduit ends and said leg conduit.

16. The apparatus as defined in claim 10 wherein said filter means separately filters particulate metal and ions of at least one heavy metal, and said particulate metal filter means is separate from and upstream of said heavy metal ion filter means.

17. The apparatus as defined in claim 12 including a housing having a pair of porous walls between which is adapted to be disposed said filter means.

18. The apparatus as defined in claim 14 including a housing having two pair of porous walls between each of which is adapted to be disposed a separate one of said filter means.

19. The apparatus as defined in claim 18 wherein said filter means for filtering particulate metal is upstream of said filter means for filtering metal ions.

20. The apparatus as defined in claim 19 wherein said conduit means includes a generally T-shaped conduit portion defined by an arm conduit and a leg conduit joined to said arm conduit medially of ends of the latter, said leg conduit being in fluid communication with said filter means, and said adjustable metering valve means being disposed to adjust the rate of flow of the bled-off liquid portion between one of said arm conduit ends and said leg conduit.

* * * * *